United States Patent [19]

Boesten et al.

[11] Patent Number: 5,087,753
[45] Date of Patent: Feb. 11, 1992

[54] PROCESS FOR RECOVERING α-AMINOALCOHOLS

[75] Inventors: Wilhelmus H. J. Boesten, Sittard; Catharina H. M. Schepers, Stein; Mathieu J. A. Roberts, Schinnen, all of Netherlands

[73] Assignee: Stamicarbon B.V., Geleen, Netherlands

[21] Appl. No.: 585,271

[22] Filed: Sep. 19, 1990

Related U.S. Application Data

[63] Continuation of Ser. No. 290,357, Dec. 27, 1988, abandoned.

[30] Foreign Application Priority Data

Dec. 30, 1987 [NL] Netherlands ............... 8703159

[51] Int. Cl.$^5$ ............... C07C 209/60; C07B 57/00
[52] U.S. Cl. ............... 564/302; 564/303; 564/374; 564/381; 564/503
[58] Field of Search ............... 564/302, 303, 503, 164, 564/381, 374

[56] References Cited

U.S. PATENT DOCUMENTS 4,172,846 10/1979 Boesten ............... 564/164

OTHER PUBLICATIONS

Evans et al., "Asymmetric Glycine Enolate Aldol Reactions: Synthesis of Cyclosporine's Unusual Amino Acid, MeBmt[1]," *J. Am. Chem. Soc.* 108:6757-61 (1986).

Primary Examiner—Glennon H. Hollrah
Assistant Examiner—B. Bembenick
Attorney, Agent, or Firm—Cushman, Darby & Cushman

[57] ABSTRACT

Process for recovering α-aminoalcohols by extraction from aqueous solutions, in which process an aromatic aldehyde is added at elevated pH to an aqueous solution of an aminoalcohol in an at least equimolar amount in respect of the aminoalcohol, the resulting mixture is converted with formation of the Schiff base of the aldehyde and the aminoalcohol and the aqueous solution is subsequently extracted using a water-immiscible organic solvent, upon which the Schiff base in the resulting extract is hydrolized and the α-aminoalcohol or a salt thereof is recovered.

13 Claims, No Drawings

PROCESS FOR RECOVERING α-AMINOALCOHOLS

This is a continuation of application Ser. No. 07/290,357, filed on Dec. 27, 1988, which was abandoned upon the filing hereof.

The invention relates to a process for recovering α-aminoalcohols by extraction from aqueous solutions. The invention particularly relates to a process which makes it possible for α-aminoalcohols to be extracted from aqueous solutions on a technical scale. The process is particularly important for recovering optically pure D- or L-α-aminoalcohols such as, for instance, D- or L-phenylglycinol, -phenylalaninol, -valinol, -methionol, etc.

Optically pure α-aminoalcohols are important as intermediates, for instance for pharmaceuticals and agrochemicals. Thus it has been found, for instance, that the aminoalcohols derived from natural amino acids are strong, reversible inhibitors for the protein synthesis (see, for instance, B. J. Hansen et al., J. Biol. Chem. 247, p. 3854 (1972)).

The reduction of amino acids or of esters thereof to form alcohols is in fact already a classical chemical process. P. Karrer et al. described as early as in 1921 the reduction of α-amino acid esters with sodium and alcohol to form α-aminoalcohols (P. Karrer et al., Helv. 4, p. 76 (1921)). Much synthetic research has since been carried out on such reductions and many reductants and reduction conditions have been tried out to obtain better yields and less racemization. Good results were obtained with lithiumaluminiumhydride in ether (see, for instance, P. Karrer et al., Helv. XXXI, pp. 1617–1623 (1948)).

In U.S. Pat. No. 3,935,280 the reduction is described of amino acids to aminoalcohols using borontrifluoride and diborane, a borane/ether- or borane/organic sulphide complex. The relevant aminoalcohol is obtained in the process after hydrolysis of the reaction mixture. The borontrifluoride apparently first forms a complex with the amino group of the amino acid, upon which the carboxylic acid group is subsequently reduced by the borane compound. The relevant reaction can be carried out in many solvents. In the recovery from the aqueous medium a great many extraction steps have been found necessary in order to come to a good isolated yield (60–85%). The high solubility of the aminoalcohols in water and the unfavourable distribution coefficient make their recovery from aqueous media a laborious process, as appears from the repeated extractions required. See, for instance, also D. A. Evans et al. in J.A.C.S. 108, p. 6758 (1986) the recovery of (2S)-2-amino-3-phenylpropanol by five extractions is described.

The object of the invention therefore is to provide a simple process for recovering α-aminoalcohols by extraction from aqueous media without having to make use of laborious repeated extractions or of a continuous extraction process hard to realize on a technical scale.

It has now been found that the recovery of (optically active) α-aminoalcohols from aqueous media proceeds with high yields and in a simple manner by first converting the α-aminoalcohol in the aqueous medium into a Schiff base, extracting it from the aqueous phase and subsequently hydrolizing it with acid, the aminoalcohol being precipitated in the process in the form of salt.

The process according to the invention for recovering an α-aminoalcohol by extraction from an aqueous solution is characterized in that at elevated pH an aromatic aldehyde is added to an aqueous solution of an aminoalcohol, the resulting mixture is converted with formation of the Schiff base of the aldehyde and the aminoalcohol, the resulting aqueous solution is extracted using a water-immiscible organic solvent, upon which the Schiff base in the resulting extract is hydrolized and the α-aminoalcohol or a salt thereof is recovered.

The object of the invention is thus achieved in a simple manner, with the recovery yield at least as high as in the processes customary so far.

Aqueous solutions of α-aminoalcohols are obtained, for instance, in the preparation of these compounds by the reduction of α-amino acids or esters thereof with sodiumboronhydride, lithiumaluminiumhydride, or combinations of borontrifluoride with diborane, borane/ether- or borane/organic sulphide complexes. After the reduction and the hydrolysis of the excess of reductant with, for instance, sodium hydroxide, the reaction mixture obtained is often pre-purified by distillation, for instance by the azeotropic removal of water and organic solvent, such as tetrahydrofuran, before starting the extraction of the aminoalcohol. Up to this point there is generally no difference between the processes according to the state of the art and the process according to the invention. In the reduction step, however, various variants of the known mode of realization do exist.

In the process according to the invention the pH of the aqueous solution obtained is now increased, if still necessary, to preferably beyond 9.5 and an aromatic aldehyde is added to the aqueous phase, preferably in at least an equimolar amount in respect of the amount of α-amino acid or ester thereof used in the reduction. The formation of the Schiff base of the α-aminoalcohol and the aromatic aldehyde proceeds quantitatively during the stirring of the reaction mixture at a temperature of 0°–100° C. until the reactant, which is present in a substoechiometric amount, is fully converted. The rate at which this reaction proceeds depends, of course, on the chosen reaction conditions. At a pH lower than 9.5 there is usually no quantitative formation of a Schiff base. Quantitative formation of a Schiff base is possible only if the amino group of the aminoalcohol is unprotonated, i.e. only at pH values equal to or higher than the natural pH of the aminoalcohols. At a pH higher than 13 undesired side reactions often take place, particularly at higher temperatures, such as disproportionation of the aldehyde used. In so far as pH is concerned, preference is given to values of between 10.5 and 13. The chosen temperature will preferably be between 40° to 60° C., the more so because, without further cooling, the starting mixture obtained in the preliminary step after the azeotropic removal of water and organic solvent can then be used. The time during which the mixture is stirred for the formation of the Schiff base will usually be at least 10 minutes. With shorter stirring times there is usually no complete conversion. Usually stirring takes place for 10–120 minutes. Under the preferred conditions in respect of pH and temperature the stirring time is 20–80 minutes. In order to achieve complete conversion of α-aminoalcohol into Schiff base, the amount of the aromatic aldehyde must at least be equivalent to the amount of α-aminoalcohol. Indeed, with subequimolar amounts of aldehyde in respect of the α-aminoalcohol Schiff base is formed, but in the case the excess of α-aminoalcohol continues to be in solution without subsequently being properly recovered. The advantage of the process operation using at least an equimolar amount of aromatic aldehyde in respect of the α-aminoalcohol is that the aminoalcohol is recovered via extraction of the Schiff base in a very high, virtually quantitative yield.

In practice a small excess of aromatic aldehyde calculated on the α-aminoalcohol is already sufficient to obtain an excellent result. As the reduction of the α-amino acid or of the ester thereof to the α-aminoalcohol does not proceed quantitatively, this small excess is automatically obtained if an equimolar amount of aldehyde is chosen in respect of the starting quantity of the α-amino acid or ester thereof to be reduced.

The aromatic aldehydes used may be benzaldehydes substituted or not substituted with alkyl, aryl, halogen, alkoxy, dialkylamino. Preference is given to the use of benzaldehyde on account of the price, availability and handling.

By stirring, under the above-mentioned conditions, the mixture in which the Schiff base is formed an aqueous phase is obtained (or possibly even a two-phase system if a much larger excess of benzaldehyde is used) from which the Schiff base can subsequently be extracted by means of a water-immiscible organic solvent in which the Schiff base dissolves well.

In the process one extraction will in principle suffice, because it has been found that this will already give a very high yield of extraction. However, if so desired, the extraction can be repeated once again in order to remove the final residue of the Schiff base from the aqueous phase.

As extractant for the Schiff base various organic solvents can be used, for instance esters (for instance ethyl- or butyl-acetate), ketones (for instance methylisobutylketone), ethers (such as methyl-t-butyl ether) and chlorinated hydrocarbons (for instance dichloroethane), but also benzaldehyde itself can be used as extractant. This last-mentioned use can already be realized by applying a multiple excess of benzaldehyde in the formation of the Schiff base.

The extractant used is preferably a solvent for the Schiff base, in which, when the Schiff base is hydrolized, it is possible for the aminoalcohol to be well separated off in the form of a derivative. As such esters such as, for instance, ethyl- and butylacetate are highly suitable.

The hydrolysis of the Schiff base in the extractant can be carried out in the manner known in the art, particularly by acidifying the solution with, for instance, hydrochloric acid. In a first mode of realization it is to be preferred not to allow the amount of water in this solution to be much larger than the equivalent amount required for the hydrolysis, because otherwise the crystallization of the salt formed will be interferred with. A manner to add the acid without much water is, for instance, by the dropwise addition of acid-saturated extractant or by metering in, for instance, gaseous hydrogen chloride. If necessary, a limited amount of water is yet to be added in order to make the hydrolysis complete.

In another mode of realization, the acid, for instance hydrochloric acid, can be added in the form of an aqueous solution. It is true that in that case there is no question of directly separating off the salt of the α-aminoalcohol, but now good separation can be achieved by removing the surplus water by azeotropic distillation. Here again, owing to the favourable azeotrope formation during distillation, the esters are highly suitable as solvent.

As explained above, a very good recovery of α-aminoalcohols from an aqueous medium in one extraction step is realized by applying the process according to the invention. As appears from literature (and also from the comparative example mentioned by applicant hereinafter), direct extraction of the free α-aminoalcohols from aqueous solutions requires a great many (5 or 6) successive extractions (ethylacetate, dichloromethane or ether) to obtain a good extraction yield (60–85%). On an industrial scale this is hardly feasible.

The process according to the invention provides a technically simpler process for recovering α-aminoalcohols and, moreover, achieves the same extraction yields as those of the direct extraction method, and often even better. The process is particularly suited for recovering optically pure D- or L-α-aminoalcohols.

The invention will be further elucidated by means of the following examples without, however, being limited thereto.

Experimental Section

The examples all start at the moment when the desired α-aminoalcohol in aqueous medium has been obtained. This can be achieved, for instance, via the reduction process below. The yields described, including extraction, have been calculated on the starting compound to be reduced.

Recipe for reducing an α-amino acid to an α-aminoalcohol

Into a (three-necked) two-liter flask with stirrer and heating device is introduced (a solution of) 0.25 mole of an α-amino acid in 200 ml tetrahydrofuran or dioxane and added to it is 60 ml borontrifluoride-etherate (0.5 mole $BF_3$), upon which the mixture is heated under reflux (c. 75° C.) for 45 minutes. The mixture is subsequently cooled in the flask to 3° C. (with ice/in an ice bath) and to the cooled reaction mixture 19 g sodiumboronhydride (solid, 0.5 mole) is added in one step. A substantial amount of gas is formed, the temperature of the mixture rising in consequence of the exothermal reaction to c. 25° C. As soon as the rise in temperature is virtually over, heating takes place to reflux and the reaction is continued for two more hours. All amino acid is then converted.

The excess of sodiumboronhydride still present is now decomposed by carefully adding 200 ml water dropwise. In order to dissolve all solid present, 150 ml 5 n sodiumhydroxide is added and heating of the mixture takes place under reflux for 1.5 more hours. Finally, 200 ml water is added once again and the azeotrope tetrahydrofuran- or dioxane-water is distilled off in vacuum (c. 50° C., 12 mm Hg). The total amount of distillate is c. 240 ml. The aqueous residue is subsequently used as starting product for recovering the α-aminoalcohol.

EXAMPLE I (L-phenylglycinol)

The above-mentioned reduction recipe was carried out proceeding from 37.8 g (0.25 mole) L-phenylglycine in 200 ml dioxane.

In order to recover the aminoalcohol formed, which remained in the aqueous residue, 25.4 ml benzaldehyde (0.26 mole) was added dropwise at a pH of 10.5 and this mixture was stirred for one more hour at 50° C.

The resulting mixture was subsequently extracted using 250 ml butylacetate. The organic phase was then, for neutralization purposes, washed with 50 ml water and separated off again.

The now resulting organic phase was distilled in vacuum for removing the water yet dissolved (50° C., 12 mm Hg). Subsequently, to the organic phase thus dried 4.5 ml water was added (corresponding with the theoretically calculated amount required for the hydrolysis of the quantitatively formed Schiff base of benzaldehyde and L-phenylglycinol), upon which to the mixture thus obtained butylacetate saturated with gaseous hydrogen chloride was added dropwise at room temperature. A total amount of 350 ml of it was metered.

A fine white precipitate was formed, which was filtered off, washed with ether and dried. The dry product obtained weighed 35.8 g and was on analysis found to be the hydrochloric acid salt of L-phenylglycinol. The optical purity was calculated at $[\alpha]^{20}_D = +24.3$ ($C=1$, $H_2O$), which corresponds with c. $+25$ with $C=8.79$, $H_2O$. For comparison, the value in literature (Dict. of Org. Compounds, Vol. I, p. 309, Chapman and Hall, New York, 5th ed., 1982) is $[\alpha]^{17}_D = +25.3$ ($C=8.79$, $H_2O$).

The yield of 35.8 g corresponded with 0.206 mole and constituted a yield after recovery, including hydrogenation, of 82.5%.

EXAMPLE II (L-phenylalaninol)

The reduction process described above was carried out starting from 41.2 g L-phenylalanine (0.25 mole) in 200 ml tetrahydrofuran. After distilling off the azeotrope tetrahydrofuran-water in vacuum (50° C., 12 mm Hg), c. 650 ml distillation residue was obtained. At a pH of 10.5, 27.5 ml benzaldehyde (0.28 mole) was added to it in drops, upon which the mixture was stirred for one hour at 50° C. The resulting aqueous phase was extracted at this temperature with 250 ml butylacetate. The organic phase was subsequently washed with 50 ml water and separated off again.

Subsequently, 25 ml concentrated hydrochloric acid (36% (wt)) was added in drops during stirring, upon which once again 250 ml butylacetate was added in order to come to a proper crystallization of the salt. (NB: In principle this amount of butylacetate can be added already in the extraction step without affecting the result). The azeotrope butylacetate/water was subsequently distilled off in vacuum (50° C., 12 mm Hg). A total amount of 290 ml distillate was collected, of which 25 ml water. At the end of the distillation process a fine white precipitate started crystallizing out in the residue. After cooling of the residue the precipitate formed was filtered off, washed with 50 ml ether and dried.

The product thus isolated (41.3 g) was found to be the hydrochloric acid salt of L-phenylalaninol, which corresponded with 0.233 mole, or a yield of 89.5%.

The optical purity was determined at $[\alpha]^{23}_D = -19.2$ ($C=1$, 1 n HCl).

In J. Chem. Soc. Chem. Comm. 1979, p. 876, $[\alpha]^{23}_D = -18.0$ ($C=0.98$, 1 n HCl) is given.

COMPARATIVE EXAMPLE

In order to compare the extraction yield of the process according to the invention, in which the extraction is carried out indirectly via a Schiff base, with the corresponding extraction yield of the direct extraction process, 200 ml of a 7%-(wt) solution of L-phenylglycinol in water was prepared. This concentration is in the order of magnitude of the concentration that occurs, in the process according to the invention, in the distillate residue (after reduction and further processing of the reduction mixture), i.e. in the starting product for the extraction.

a. 100 ml of this 7%-(wt) solution of L-phenylglycinol in water was extracted with, each time, 50 ml ethylacetate. After the first extraction 70% of the L-phenylglycinol was still present in the aqueous phase. After five extractions in all using 50 ml ethylacetate 70% of the original amount of L-phenylglycinol was found to have been incorporated in the organic phase.

b. The same test was carried out with the other 100 ml of the 7%-(wt) L-phenylglycinol solution, but now 50 ml dichloroethane was used each time. After the first extraction only 18% and after five extractions in all only 60% of the original amount of L-phenylglycinol was incorporated in the organic phase.

It should be noted in this connection that the extraction yields in the comparative example (resp. 70 and 60% after five extractions) must be set off against the yields of examples I and II of resp. 82.5 and 89.5% overall, including reduction step.

We claim:

1. Process for recovering an α-aminoalcohol by extraction from an aqueous solution comprising the following steps: at elevated pH an aromatic aldehyde is added to an aqueous solution of an aminoalcohol, the resulting mixture is converted with formation of the Schiff base of the aldehyde and the aminoalcohol, the resulting aqueous solution is extracted using a water-immiscible organic solvent, upon which the Schiff base in the resulting extract is hydrolized and the α-aminoalcohol or a salt thereof is recovered.

2. Process according to claim 1, characterized in that the aromatic aldehyde is added at a pH higher than 9.5.

3. The process of claim 2 wherein said pH is between 10.5 and 13.

4. Process according to claim 1, characterized in that the mixture of the aqueous solution of the aminoalcohol and the aromatic aldehyde is converted for at least 10 minutes.

5. The process of claim 4 wherein said conversion is for 10 to 120 minutes.

6. Process according to claim 4, characterized in that the mixture of the aqueous solution of the aminoalcohol and the aromatic aldehyde is converted for 20 to 80 minutes.

7. Process according to claim 1, characterized in that the stirring is carried out at a temperature of 0°-100° C.

8. The process according to claim 7 wherein said temperature is 40°-60° C.

9. Process according to claim 1, characterized in that the aldehyde is used in at least an equimolar amount in respect of the aminoalcohol.

10. Process according to claim 9, characterized in that a small excess of the aromatic aldehyde is applied in respect of the aminoalcohol.

11. Process according to claim 1, characterized in that the water-immiscible organic solvent is an ester.

12. Process according to claim 1, characterized in that the aromatic aldehyde is benzaldehyde.

13. Process for recovering an α-aminoalcohol by extraction from an aqueous solution, comprising the following steps: at elevated pH an aromatic aldehyde is added to an aqueous solution of an aminoalcohol, said aldehyde being used in at least an equimolar amount with respect to the aminoalcohol; the resulting mixture is converted with formation of the Schiff base of the aldehyde and the aminoalcohol; and the resulting aqueous solution is extracted using a water-immiscible organic solvent, upon which the Schiff base in the resulting extract is hydrolized and the α-aminoalcohol or a salt thereof is recovered.

* * * * *